US008551016B2

(12) United States Patent
Slowey et al.

(10) Patent No.: US 8,551,016 B2
(45) Date of Patent: Oct. 8, 2013

(54) MULTI COMPARTMENT BODY PART SCRAPING FLUID COLLECTION DEVICE

(75) Inventors: Paul Slowey, Vancouver, WA (US); Jason Giddings, Forest Grove, OR (US)

(73) Assignee: Oasis Diagnostics Corp., Vancouver, WA (US)

( * ) Notice: Subject to any disclaimer, the term of this patent is extended or adjusted under 35 U.S.C. 154(b) by 250 days.

(21) Appl. No.: 12/628,893

(22) Filed: Dec. 1, 2009

(65) Prior Publication Data

US 2010/0137741 A1    Jun. 3, 2010

Related U.S. Application Data

(60) Provisional application No. 61/118,911, filed on Dec. 1, 2008.

(51) Int. Cl.
*A61B 5/00*    (2006.01)
(52) U.S. Cl.
USPC ......................................................... 600/573
(58) Field of Classification Search
USPC .................. 600/562, 569, 572, 570, 571, 573
See application file for complete search history.

(56) References Cited

U.S. PATENT DOCUMENTS

| | | | | |
|---|---|---|---|---|
| 3,766,907 | A | * | 10/1973 | Muenzer ........................ 600/562 |
| 3,800,781 | A | * | 4/1974 | Zalucki .......................... 600/562 |
| 3,838,681 | A | | 10/1974 | Dalton |
| 4,741,346 | A | | 5/1988 | Wong et al. |
| 4,951,684 | A | | 8/1990 | McMillan |
| 5,063,026 | A | * | 11/1991 | Wong ............................. 600/572 |
| 5,422,273 | A | * | 6/1995 | Garrison et al. ............ 435/307.1 |
| 5,919,146 | A | | 7/1999 | Propp |
| 6,200,276 | B1 | | 3/2001 | Biesel et al. |
| 6,299,842 | B1 | | 10/2001 | Kozak et al. |
| 6,312,395 | B1 | * | 11/2001 | Tripp et al. ..................... 600/572 |
| 6,840,911 | B2 | * | 1/2005 | Sangha .......................... 600/582 |
| 7,257,991 | B2 | | 8/2007 | Wickstead et al. |
| 2003/0021736 | A1 | | 1/2003 | Kang et al. |
| 2004/0181170 | A1 | * | 9/2004 | Wallach ......................... 600/569 |
| 2004/0260194 | A1 | | 12/2004 | Bayer et al. |
| 2005/0096563 | A1 | | 5/2005 | Liang |
| 2006/0047292 | A1 | | 3/2006 | Reed |
| 2006/0149164 | A1 | | 7/2006 | Lee et al. |
| 2007/0208274 | A1 | * | 9/2007 | Ostrowski et al. ............ 600/573 |
| 2008/0118397 | A1 | | 5/2008 | Slowey et al. |
| 2009/0012425 | A1 | | 1/2009 | Dodge et al. |
| 2009/0038416 | A1 | | 2/2009 | Bonner |
| 2009/0208371 | A1 | | 8/2009 | Hannant |

OTHER PUBLICATIONS

International Search Report for PCT/US2011/023370.
International Preliminary Report on Patentability for PCT/US2011/023370.

* cited by examiner

*Primary Examiner* — Max Hindenburg
(74) *Attorney, Agent, or Firm* — Rylander & Associates PC; Kurt M. Rylander; Mark E. Beatty

(57) ABSTRACT

An embodiment is a fluid sample collection system. More specifically, an embodiment is a fluid sample collection system to facilitate collection of biological specimens and particularly to facilitate collection of saliva, urine, and stool specimens from human or animal species for the purpose of extracting purified DNA and/or RNA.

10 Claims, 5 Drawing Sheets

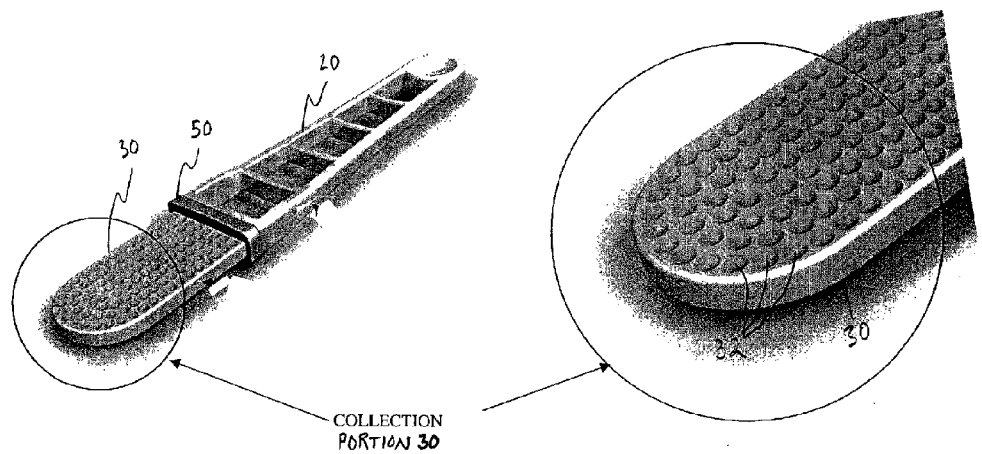
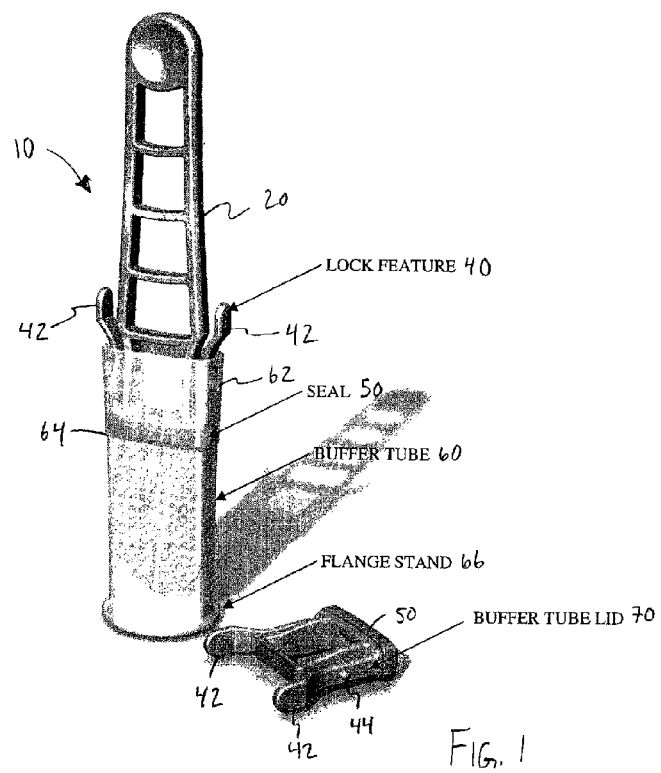
FIG. 1

FIG. 5
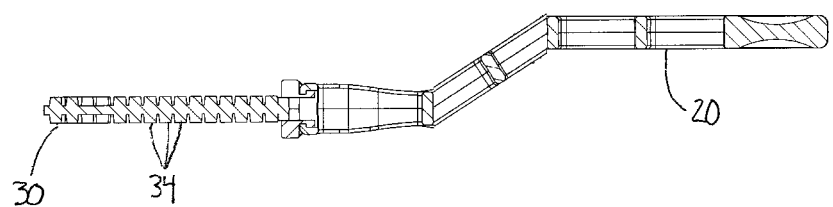
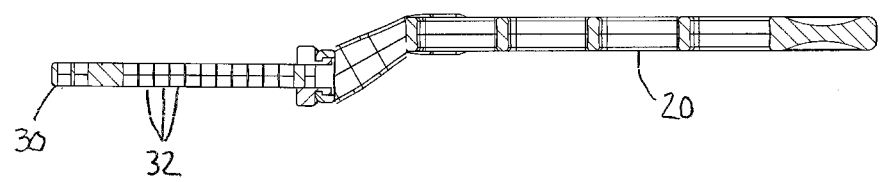
FIG. 6
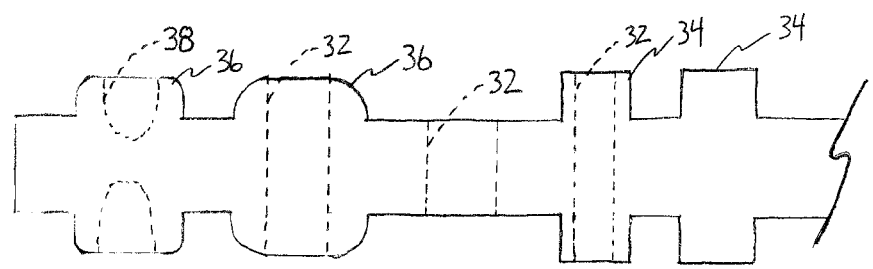

MULTI COMPARTMENT BODY PART SCRAPING FLUID COLLECTION DEVICE

CROSS-REFERENCE TO RELATED APPLICATION

This application claims priority to U.S. Provisional Patent Application Ser. No. 61/118,911 filed Dec. 1, 2008, which is incorporated herein by reference.

FIELD OF THE INVENTION

The present invention relates to devices for collecting body fluid samples by scraping the surface of a body part.

BACKGROUND

Over the last few years there has been a tremendous growth in the area of salivary diagnostics, prompted in part by efforts from the National Institutes of Health (NIH) and its National Institute of Dental and Craniofacial Research (NIDCR) division to promote the development of non-invasive technologies for the diagnosis of diseases and measurement of specific analytes or molecules in saliva or oral fluid samples. These agencies have made funding available for the development of novel, innovative tools including microarrays, lab-on-a-chip, lateral flow, ELISA and other technologies using saliva and other non-invasive sampling methodologies. Other reasons for the increased interest in salivary diagnostics include the development of important new technologies for both the collection and testing of oral fluids and improvements in the manufacturability of such devices.

There are several successful corporate stories in salivary diagnostics that are also prompting other companies to search out opportunities in non-invasive testing. For instance, it is now possible to detect HIV antibodies from oral specimens at the point-of-care using the OraQuick® HIV 1/2 rapid antibody test (OraSure Technologies, Bethlehem Pa., USA) with greater than 99% sensitivity and specificity. This company is currently proceeding with an FDA submission that would allow consumers to purchase such a test over the counter in a pharmacy.

In the United States millions of oral specimens are collected and processed in the Public Health and insurance market sectors for HIV antibodies, cotinine (nicotine) for smoking and cocaine as part of a "risk assessment" profile. Additionally, options for testing Federal employees for a range of abused drugs using non-invasive methods including saliva are readily accepted by SAMHSA, the Substance Abuse Mental Health Services Administration (the US Government body responsible for drug testing in the Federal workplace). Such testing is also common in the workplace environment where corporations in the US (and other parts of the world) use saliva as part of pre-employment and random drug testing policies.

General wellness is monitored by testing various steroid hormones in the laboratory. Home collection using a standardized saliva collection kit is common place and a large number of testing laboratories have appeared offering a multitude of test options for the "worried well". Tests include a range of male and female hormones including testosterone, estradiol, progesterone, cortisol and others. In these situations no "diagnosis" is provided on collected samples. Instead, a Medical Director from the laboratory will provide an indication of the levels of a specific target analyte in the saliva and make recommendations on suitable lifestyle changes or perhaps an imminent visit to the doctor.

The future for saliva testing also holds great promise since the publication of the entire salivary proteome by the Human Saliva Proteome Consortium, a group headed by Dr. David Wong from UCLA. The widespread publication of the identity of 1,166 proteins potentially implicated in disease progression will lead to the rapid growth in new applications for salivary diagnosis. Already in development are a diagnostic device for the rapid detection of the drug phenytoin, which uses a surface plasma resonance imaging instrument, an oral fluid Nanosensor test that measures four oral fluid markers as an indication of oral cancer and a lab-on-a-chip technology for point-of-care detection of salivary biomarkers in periodontitis, among a number of others. An excellent review of these and other new applications for oral fluid diagnostics was published following a landmark meeting of many researchers in the field at Lanier Lakes, Ga. USA in October 2006. The monograph published following the meeting is available from the New York Academy of Sciences.

Tools for oral fluid diagnosis may be categorized as one of two types. The first is diagnostic devices providing an immediate diagnosis or test result, so-called "point-of-care" or "near-patient" tests. This category includes the manual OraQuick® rapid HIV 1/2 antibody test that employs lateral flow immunochromatographic technology and the prototype Oral Fluid Nanosensor (OFNASET) Test device from Dr. David Wong's UCLA laboratory, which relies on microfluidics, nanotechnology in a hand-held reading device to potentially screen for oral cancer. This technology detects a series of four salivary molecular RNA markers. Another example among many others is a rapid point-of-care drug screening technology called RapiScan® from Cozart Biosciences (Abingdon, UK), which is used to screen would be drug offenders at the roadside using saliva samples. Many other rapid diagnostic products exist which require saliva sampling or testing, but such products are outside the scope of this application.

The other side of the market for salivary diagnostics involves the collection of oral fluids and the subsequent transportation of the samples to a laboratory, or other remote site where the testing is performed. Again many examples exist. Examples include the collection of oral samples for HIV testing for Public Health and also for insurance risk assessment, where oral specimens are collected using the OraSure® Oral Fluid Collection Device (OraSure Technologies, Bethlehem Pa., USA) and sent to a laboratory. Typically, specimens are analyzed using traditional ELISA technology for the detection of HIV, cotinine (nicotine), cocaine and others. Others include collection of saliva specimens for drug testing in the workplace environment for pre-employment purposes or random drug testing. In such situations saliva is collected using one of a number of available commercial saliva collection devices (including Intercept™ from OraSure Technologies, Bethlehem Pa., USA, Quanti-SAL™ from Immunalysis Corporation, Pomona Calif., USA, Aware Messenger™ from Calypte Biomedical, Lake Oswego, Oreg. USA and Salivette®, Sarstedt, Germany among others) then sent to a laboratory where a battery of drug tests including marijuana (THC), cocaine, opiates (heroin), methamphetamine, amphetamine, and phencyclidine is tested on the processed saliva. Similar practices are observed in Federal workplace and military drug testing environments.

A small industry has emerged for salivary hormone testing where laboratories provide saliva collection kits and a test menu for home users. Clients expectorate into a tube that is subsequently sent to a laboratory. As part of the service subjects are able to request testing for various steroid hormones as part of a general wellness screening panel. The results provide an indication of general health and wellness, without providing any definitive diagnosis.

Very recently a new industry has emerged for "personal genome" testing in what is termed the "consumer genetics" market. In this area saliva or buccal cell swab samples are collected in the home and sent to a laboratory and tested for specific genetic markers and single nucleotide polymorphisms (SNPs) that provide information on the parentage of the individual in question, predisposition to specific diseases, ancestry and other genetic information. The number of companies in this area is rapidly growing but at this time, the recognized market leading companies are 23andMe, Navigenics, DeCode Genetics, Knome, Illumina, and Sciona. The convenience and non-invasiveness makes saliva very attractive for home testing/home collection products. Other applications in this market sector will be addressed in further detail below.

In general, multi-purpose saliva collection is facilitated using one of a number of commercially available saliva collection devices or by expectoration ("spitting") into a sample receptacle. A number of devices are now available to collect specimens and these include the OraSure® device (OraSure® Technologies), Aware Messenger™, Salivette, Omni•SAL® (Stat-Sure Diagnostics, Framingham, Mass., USA), ORA-COL (Malvern Medical Developments, UK), Cozart Oral Swab (Cozart BioSciences, Abingdon, UK) and the Versi•SAL® device (Oasis Diagnostics® Corporation, Vancouver, Wash. USA). With the exception of the Versi•SAL® device, which provides the opportunity to use multiple absorbent materials, customized to specific applications, these products have limited applications. This is mainly due to limitations in the number and type of absorbent materials used to perform the saliva collection operation. While each of the above methodologies may be considered appropriate for certain applications in salivary testing, none of these devices is appropriate for the collection, stabilization, transportation and extraction of purified DNA from saliva. This in turn has restricted the use of salivary DNA for "downstream" applications particularly the potential use of saliva specimens for molecular diagnostic testing.

Molecular diagnostics is one of the fastest growing areas in the area of clinical and animal diagnostics. The current market for molecular diagnostics is estimated to be $3.2 billion (2007 figures) and forecast to reach $5.4 billion by 2012. In this area of clinical diagnostics traditional blood testing is by far the current method of choice. In current protocols, specimens are collected in a blood tube, usually by a trained phlebotomist, and sent to the laboratory. Upon receipt at the laboratory, the sample is initially separated from unwanted blood by-products then further purified prior to analysis. Blood samples contain potentially infectious agents and the cost of transportation can be expensive. In addition, all samples must be treated as infectious waste and disposed of according to recognized safety standards, which can also be costly. If a device was available to collect salivary DNA for clinical diagnostic testing this would offer several advantages over current blood testing algorithms and would be welcomed in clinical practice as a step forward. From the patient's perspective it would eliminate painful blood draws associated with current testing. In addition it would eliminate the need for a trained phlebotomist to draw the blood sample, as well as alleviate any potential for infection from tainted blood samples. Overall, saliva sampling is generally cheaper and does not require an additional pre-treatment step (as required for blood), to separate the required salivary component prior to analysis.

As described previously, there are a number of commercially available saliva collection devices on the market. In most cases, these devices incorporate some sort of absorbent material that is used to collect the saliva specimen. The sample is subsequently removed from the absorbent material using methods such as squeezing, centrifugation or simply soaking in a buffer to solubilize the target analytes. These devices work well for the collection of certain molecules such as infectious disease antibodies (including HIV, hepatitis B, hepatitis C and others), hormones, cancer biomarkers and drugs, for instance, but none of these may be applied to the collection and retrieval of DNA (Deoxy Ribonucleic Acid) or RNA (Ribo Nucleic Acid), which requires a device with very specific performance characteristics. This is due to an inherent property of current devices to bind DNA and RNA moieties to the fibers of the absorbent material used to collect the specimen. DNA binds tightly to the fibers and is not easily removed. Any effort to remove the DNA, cells using reagents, organic solvents usually results in denaturation of the DNA molecules and subsequently observed recoveries are poor.

Some of the above limitations have been overcome in a few devices that do successfully facilitate salivary DNA collection. Expectoration (spitting in a cup or other vessel) provides a saliva sample that can be successfully stabilized and purified through available methodologies to yield high quality DNA, and this method is in use in various testing strategies, however this method lacks adequate standardization (sample variability) and is not considered elegant or dignified.

Over the last few years other promising devices have emerged that are based upon modifications to the traditional expectoration technique. The most widely used of these is the OraGene® DNA device from DNA Genotek (Ottawa, Ontario, Canada). OraGene® is a more sophisticated way to collect saliva into a vessel to which is attached a screw-on cap. In the screw-on cap is a mixture of preservative buffers. Upon completion of the expectoration process, the cap is screwed onto the device releasing the preservative buffer, which drops into the saliva, is mixed by shaking and then acts to protect the integrity of the sample until processing and extraction can take place. The same company has recently perfected the OraGene® RNA device for the collection of RNA from oral fluid specimens. OraGene® RNA applies the same basic principles as used in the OraGene® DNA device. Invitek Gesellschaft für Biotechnik and Biodesign mbH (Invitek, Berlin, Germany) has come up with a similar tool, SaliGene® as an alternative "spit-in-a-cup" technology, which has additional application as a collector for stool or swab specimens [when coupled with specific extraction kits for these alternate specimen types]. In the SaliGene® device, subjects expectorate into a modified collection tube until a pre-determined volume has been reached. A screw-cap with attached plunger is screwed in place and the plunger depressed causing a preservative/lysis buffer to flow into the collected saliva specimen. The sample of mixed preservatives and saliva is gently shaken then sent to a laboratory for further processing.

Researchers from Roswell Park describe the extraction of genomic DNA from saliva using the Qiagen (Hilden, Germany) QIAamp Kit on the Qiagen website. This work was reprinted from earlier work carried out in 1997. The QIAamp kit is one of a number of kits commercially available for DNA extraction from bodily fluids. In this case as in many others, expectoration was used to collect the saliva specimens.

In collecting specimens for diagnostic testing several criteria are important. Specimens need to be collected rapidly to eliminate any opportunity for sample degradation, and they must be removed rapidly from the point of collection and stabilized promptly for subsequent transportation purposes (if necessary). The specimen device used to collect saliva should be able to withstand temperature fluctuations and the rigors of shipping products by air or road allowing samples to arrive safely at the final destination laboratory, hospital or other remote facility. The sample so obtained should be stable for extended periods of time at ambient temperatures and also at −20 degrees Celsius for long-term storage.

Devices for DNA or RNA sample collection need to be robust, transportable, capable of transporting a saliva sample (or other biological fluid) containing the DNA or RNA molecules to a laboratory or other remote facility and also need to provide easy samples removal for subsequent extraction using a number of commercially available, off the shelf kits. The yield of DNA/RNA produced depends upon the particular application but should be sufficient for immediate application in testing kits provided by a multitude of manufacturers for infectious diseases, oncology, cardiovascular diseases, immunological disorders and many others. Literature reports suggest that a minimum of 10 μg of pure DNA should be collected and typically even larger quantities are required. For example, 100 μg or more of pure DNA would be a preferable sample quantity.

While the limited number of examples of salivary DNA devices described above provides methods for DNA/RNA collection and extraction, none of the above devices meet the market need for a simple, elegant, standardized and rapid method for the collection of biological fluids, with the specific purpose of extraction of DNA and RNA, for large scale implementation.

SUMMARY AND ADVANTAGES

An embodiment is a fluid sample collection system comprising a buffer tube containing a buffer, a handle, and a collection portion coupled to the handle, the collection portion including one or more holes, one or more protrusions, or a combination thereof, at least the collection portion to removably insert into the buffer tube. The fluid sample collection system may further include a locking portion coupled to the handle portion adjacent the collection portion. The locking portion may include one or more locking arms extending laterally, each of which may include one or more locking arm protrusions to engage one or more buffer tube dimples formed in the buffer tube. The locking portion may further include a seal member to substantially seal the collection portion removably inserted into the buffer tube.

The fluid sample collection system of the present invention presents numerous advantages, including: (1) facilitation of the collection of a fluid in sufficient quantity to conduct genetic testing and any other testing requiring DNA or RNA as the sample, e.g. microarrays, PCR, genotyping, and forensic sampling; (2) inexpensive construction; (3) locking and sealing feature to substantially protect the collected fluid sample; (4) rapid sample collection time; (5) simple and more elegant collection method than traditional "spit-in-a-cup" technologies; (6) more amenable for large population studies and DNA collection by the patient/subject in the home; (7) rapid collection time reduces the possibility for introduction of any "foreign" DNA; (8) incorporation of a preservative/lysis buffer capable of protecting the integrity of the sample for long periods of time Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims.

Further benefits and advantages of the embodiments of the invention will become apparent from consideration of the following detailed description given with reference to the accompanying drawings, which specify and show preferred embodiments of the present invention.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

FIG. 1 shows the fluid collection system of an embodiment.

FIG. 5 shows the fluid collection system of an alternate embodiment including an offset handle.

FIG. 6 shows example sample holes, sample posts, and sample protrusions for the collection portion of the fluid collection system of various embodiments.

REFERENCE NUMBERS USED IN DRAWINGS

Figure 2:
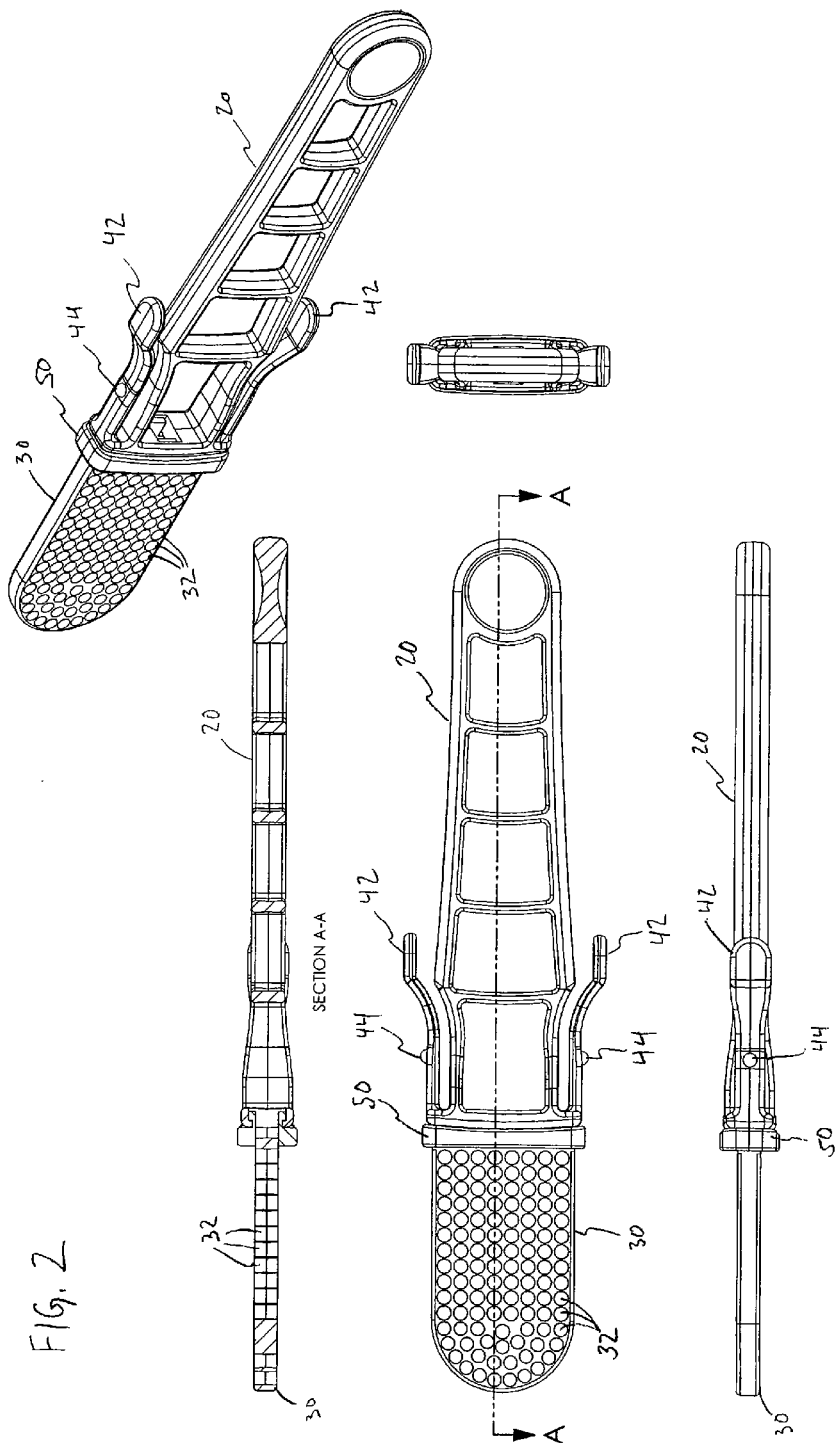
FIG. 2 shows an alternate view of the fluid collection system of FIG. 1.

Turning now descriptively to the drawings, in which similar reference characters denote similar elements throughout the several views, the figures illustrate the fluid sample collection system of an embodiment of the present invention. With regard to the reference numerals used, the following numbering is used throughout the various drawing figures:

10 fluid sample collection system
20 handle
30 collection portion
32 sample hole
34 sample post
36 sample protrusion
38 sample dimple
40 locking portion
42 locking arm
44 locking arm protrusion
50 seal member
60 buffer tube
62 buffer tube dimples
64 seal shoulder member
66 flange stand
70 buffer tube lid

DETAILED DESCRIPTION

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

As shown in FIGS. 1-6, embodiments of a fluid sample collection system 10 are provided. More specifically, an embodiment is a fluid sample collection system 10 to facilitate collection of biological specimens and particularly to facilitate collection of saliva, urine, and stool specimens from human or animal species for the purpose of extracting purified DNA and/or RNA. For example, DNA and/or RNA samples collected with the fluid sample collection system 10 of an embodiment may be purified by one of a number of established sample purification kits yielding samples sufficiently pure and of high quality to be used in immediate testing protocols for any test requiring DNA or RNA samples. The purified DNA and/or RNA may thereafter have downstream application in testing methods including molecular diagnostics (e.g., polymerase chain reaction, genotyping, personal genomic testing, microarrays, and lab-on-a-chip technologies).

As shown in FIG. 1, fluid sample collection system 10 comprises a handle 20, a collection portion 30 coupled to the handle, a locking portion 40 coupled to the handle, and a seal 50 coupled to the locking portion 40. The fluid sample collection system 10 of an embodiment further includes a buffer tube 60 into which at least the collection portion 30 may be inserted to extract and store the collected fluid sample.

The handle 20 of an embodiment may be formed with a size, shape, and/or configuration substantially suitable to be manually manipulated to scrape, swipe, and/or swab the inside of the cheek(s), along the gum line(s) under the lip(s), across the tongue and/or other saliva-bearing surface or surfaces of the human or animal to be sampled. Alternately, the handle 20 of an embodiment may be formed with a size, shape, and/or configuration substantially suitable to be manually manipulated to scrape, swipe, and/or swab urine- and/or stool-bearing sources and/or surfaces. Accordingly, in an embodiment, the handle 20 may be formed of a plastic. For example, the handle 20 may be formed at least in part from polypropylene, polycarbonate, polyethylene, polytetrafluoroethylene (PTFE), enamel, nylon, ceramic, or a combination thereof that is substantially ridged to facilitate the sample collection with the collection portion 30 coupled thereto. Further, in an embodiment, the plastic and/or other handle 20 material may be substantially heat- and/or chemical-resistant so that the fluid sample collection system 10 of an embodiment may be sterilized (e.g., in an autoclave or chemiclave) prior to sample collection.

In an embodiment, for example as illustrated by FIGS. 1-4, the handle 20 may be substantially straight. Alternately, as illustrated by FIG. 5, the handle 20 may include one or more bends or angles. For example, the handle 20 may include a single bend to form an angle in the handle 20. The handle 20 of an alternate embodiment may include two bends to form an offset in the handle 20. Further, the handle 20 may include the one or more bends at various locations along its length. More specifically, the handle 20 may include a bend substantially adjacent the collection portion 30 and/or it may include a bend adjacent the locking arms 42. The handle 20 may include an additional bend or bends along its length extending away from the collection portion 30. The one or more bends formed in handle 20 may be static bends integrally formed in the handle 20, or they may be dynamic bends that may further include a hinge, a living hinge, a pivot, or the like. The hinge and/or the pivot may include one or more springs or the like to bias the hinge and/or pivot toward a particular bend or angle. Further, if a living hinge, the properties (e.g., elasticity) of the handle 20 material may provide the bias toward a particular bend or angle.

Though not illustrated, instead of or in addition to one or more specific bends or angles, the handle 20 may include one or more areas of curvature and/or one or more areas having an arcuate shape. The one or more bends, angles, curves, and the like formed in the handle 20 of an embodiment may aid locating the collection portion 30 adjacent a desired region of sample collection. For example, the handle 20 embodiments illustrated including an offset may aid the collection of samples from the buccal region(s) (i.e., toward the inside of the cheek) of the mouth.

The handle 20 of an embodiment (e.g., straight, curved, bent, or a combination thereof) may further include score or similar feature to facilitate the breakage of the handle 20 at a particular location along handle 20. For example, once a sample has been collected with the sample portion 30, the sample portion 30 inserted into the buffer tube 60, and the sample portion 30 locked into the buffer tube 60 with locking portion 40, the sample collector may break off at least a portion of the handle 20 to decrease the size of the fluid collection system 10. The decreased size may, for example, decrease shipping materials and/or shipping costs required to ship or otherwise transport the collected sample to a laboratory or other sample analysis facility. Additionally, with at least a portion of the handle 20 detached, it may be more difficult to defeat the locking portion 40 and/or otherwise disturb the collection portion 30 within the buffer tube 60. The removal of at least a portion of handle 20 may accordingly increase the security and/or stability of the collected sample.

The collection portion 30 of an embodiment may be formed of a similar plastic as the handle 20. For example, the collection portion 30 may be formed at least in part from polypropylene, polycarbonate, polyethylene, polytetrafluoroethylene (PTFE), enamel, nylon, ceramic, or a combination thereof. In an embodiment, the collection portion 30 and the handle portion 20 are formed substantially simultaneously (e.g., in the same plastic injection mold) as the handle 20. In an alternate embodiment, the collection portion 30 may be formed at least in part from a different material than the handle portion 20 that may be more suitable for sample collection.

The collection portion 30 may include a rough texture and/or surface features to scrape, swipe, and/or swab a fluid sample from a sample source or sample substrate. For example, FIG. 2 illustrates that in an embodiment, the collection portion of an embodiment may include a plurality of sample holes 32 extending through the thickness of the collection portion 30 in which fluid and cells, as well as large molecules, may be collected. In an embodiment, the sample holes 32 may have a substantially circular cross section. Further, the diameter of the substantially circular cross section may remain substantially constant through the thickness of the collection portion. The collection portion 30 of an embodiment may include approximately 100 sample holes 32, each with a diameter of approximately 0.08 inches. The diameter of the sample holes 32 maybe adjusted to take up or otherwise collect a fluid or fluids with differing viscosity.

In an alternate embodiment, the diameter of the sample holes 32 may vary across the thickness of the collection portion 30. For example, the diameter of the sample holes 32 at the surfaces of the collection portion 30 may be larger than the diameter of the sample holes 32 approximately in the middle of the collection portion 30 thickness. Alternately, the diameter of the sample holes 32 at the surfaces of the collection portion 30 may be smaller than the diameter of the sample holes 32 approximately in the middle of the collection portion 30 thickness. In an embodiment, the collection portion 30 may include sample holes 32 with an assortment of shapes and/or sizes to accommodate a variety of sample sources and/or sample liquids.

Figure 3:
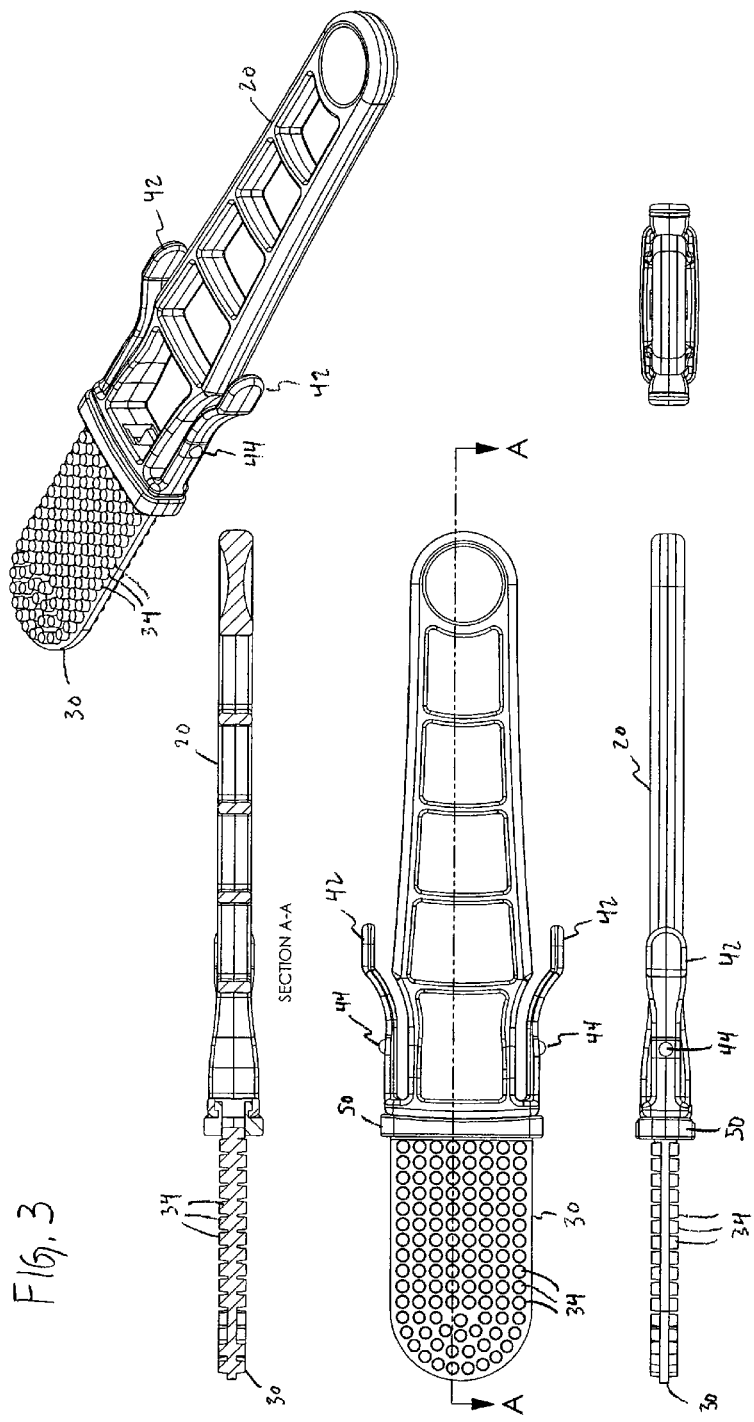
FIG. 3 shows the fluid collection system of an alternate embodiment.

FIG. 3 illustrates the collection portion 30 of an alternate embodiment. Instead of sample holes 32, the collection portion 30 may include a plurality of sample posts 34. The sample posts 34 of an embodiment may have a substantially circular cross section. For example, the sample posts 34 may be substantially shaped as cylinders (i.e., the diameter of the substantially circular cross section may remain substantially constant through the thickness of the sample posts 34). The collection portion 30 of an embodiment may include approximately 100 sample posts 34, each with a diameter of approximately 0.08 inches in diameter. The diameter of the sample posts 34 maybe adjusted to take up or otherwise collect a fluid or fluids with differing viscosity.

Alternately, the sample posts 34 may be substantially shaped as frusta (i.e., the diameter of the sample posts 34 distal from the collection portion 30 may be smaller than the diameter of the sample posts 34 at their bases adjacent the collection portion 30). In an embodiment, the collection portion 30 may include sample posts 34 with an assortment of shapes and/or sizes to accommodate a variety of sample sources and/or sample liquids.

Figure 4:
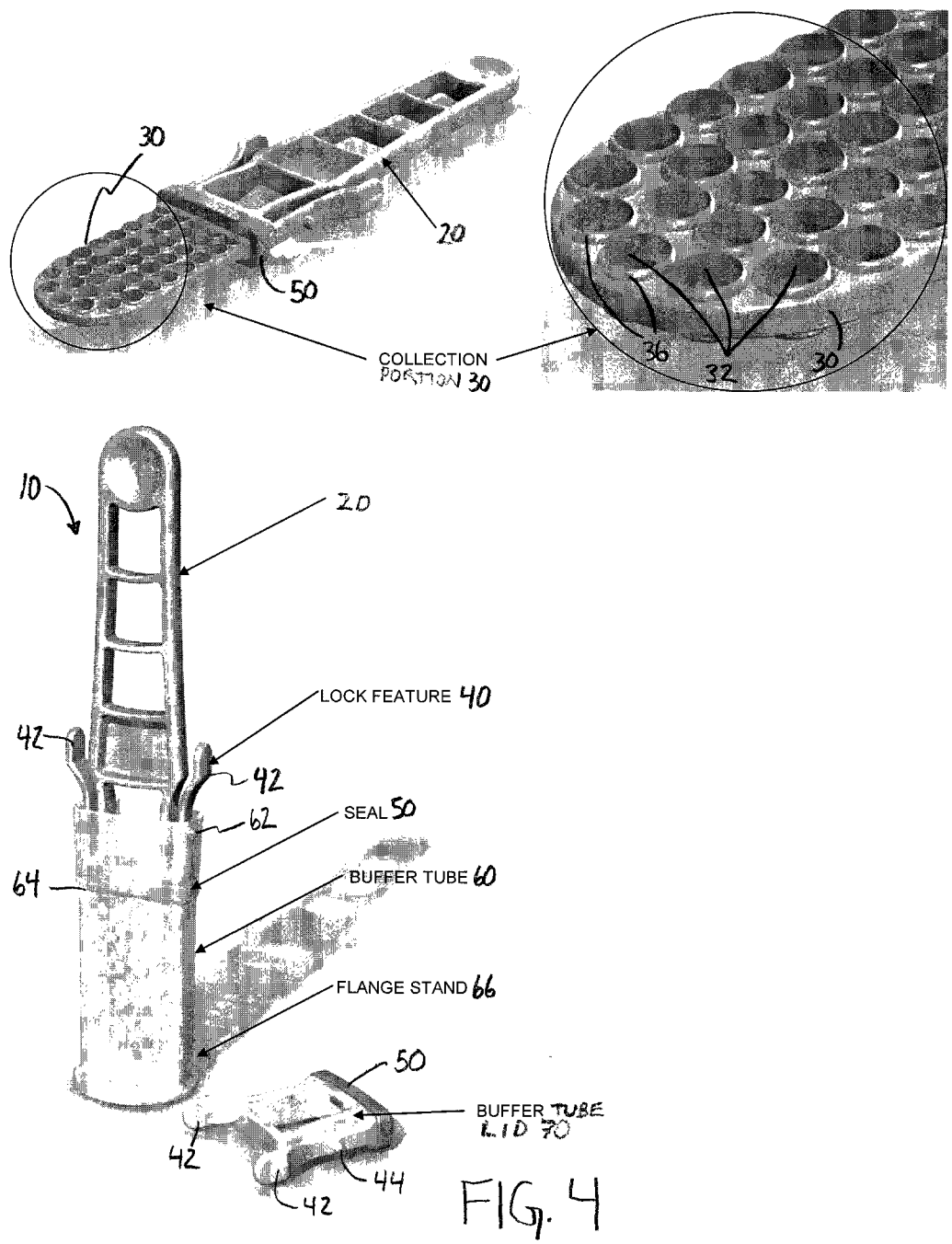
FIG. 4 shows the fluid collection system of an alternate embodiment.

FIG. 4 illustrates the collection portion 30 of an alternate embodiment including sample protrusions 36 having sample holes 32 and/or sample dimples 38 formed therein. The sample protrusions 36 may scrape or swipe a sample fluid containing surface while the sample holes 32 and/or sample dimples 38 formed therein may swab and/or otherwise the collect the sample fluid once scraped or swiped. FIG. 6 illustrates various configurations for collection portion 30 including a sample hole 32, a sample post 34, a sample post 34 including a sample hole 32, a sample protrusion 36, a sample protrusion 36 including a sample hole 32, and a sample protrusion 36 including sample dimples 38. The embodiments are not limited in this context.

The collection portion 30 of an embodiment, whether it includes sample holes 32, sample posts 34, sample protrusions 36, sample dimples 38, or a combination thereof, may be formed from a material suitable for fluid sample collection as well as cell and other bodily sample collection. For example, the collection portion 30 including sample holes 32, sample posts 34, sample protrusions 36, and sample dimples 38 in an embodiment may include a rough surface texture to facilitate the fluid sample collection as it scrapes, swipes, and/or swabs a sample fluid containing surface. More specifically, the sample posts 34 and/or sample protrusions 36 may include edges and/or surfaces that include features to increase the ability with which the collection portion 30 may scrape or rake a surface to dislodge sample fluid and sample cells. For example, the edges of the sample posts 34 and/or the sample protrusions 36 may be jagged, serrated, toothed, crenellated, or the like to scrape or rake a surface. The rough surface texture of the collection portion 30 may nevertheless not be too rough as to cause discomfort to the sample fluid and sample cell provider.

In an embodiment, the collection portion 30 material may adsorb sample fluid and may create an adsorbate at the surface of the collection portion 30 from which a sample may be collected. Alternatively, the collection portion 30 may be formed of an absorbent material into which the sample fluid may diffuse and from which a sample may be collected. Additionally or alternatively, the collection portion 30 including sample holes 32, sample posts 34, sample protrusions 36, and sample dimples 38 may be formed of a substantially hydrophilic material to attract sample fluid. As noted above, in an embodiment, at least the collection portion 30 may be formed at least in part from polypropylene, polycarbonate, polyethylene, polytetrafluoroethylene (PTFE), enamel, nylon, ceramic, or a combination thereof.

A locking portion 40 may be formed in the fluid sample collection system 10 substantially between the handle 20 and the collection portion 30. The locking portion 40 may include one or more locking arms 42 extending laterally from substantially between the handle 20 and the collection portion 30. Each locking arm 42 may further include one or more locking arm protrusions 44 to detachably engage the buffer tube 60. For example, the interior of the buffer tube 60 may include one or more buffer tube dimples 62 to detachably engage the locking arm protrusions 44. Accordingly, the detachable engagement of the locking arm protrusions 44 with the buffer tube dimples may substantially removably secure the collection portion 30 within the buffer tube 60.

The locking portion 40 of an embodiment may further include a seal member 50. The seal member 50 may detachably engage the interior of the buffer tube 60 to substantially prevent the buffer solution contained in the buffer tube 60 from leaking or otherwise escaping from the buffer tube 60. Further, as the collection portion 30 maybe at least partially immersed in the buffer solution once it has been inserted into the buffer tube 60, the seal member 50 may further substantially prevent the fluid sample contained on and/or in the collection portion 30 from leaking or otherwise escaping from the buffer tube 60. Further still, the seal member may substantially prevent contamination from entering and/or invading the buffer solution within the buffer tube 60 once the collection portion 30 as been removably inserted therein. The seal member 50 may be formed at least in part from an elastomeric material that at least partially deforms to form a substantially liquid-tight seal with the interior of the buffer tube 60.

The buffer tube 60 of an embodiment may have a substantially rigid tubular construction. In an embodiment, the cross section of the buffer tube 60 may resemble an elongated oval to substantially match the cross section of the collection portion 30 that may be removably inserted in the buffer tube 60. In addition to the buffer tube dimples 62 described above, the buffer tube 60 may further include a seal shoulder 64. The seal shoulder 64 may provide a greater surface area within the interior of the buffer tube 60 to detachably engage the seal member 50 coupled to the locking portion 40, thereby improving the seal formed between the seal member 50 and the interior of the buffer tube 60. The end of the buffer tube 60 opposite the entrance for at least the collection portion 30 and the locking portion 40 may include a flange stand 66. The flange stand 66 of an embodiment may provide a base on which the buffer tube 60 may stand to substantially prevent the spillage of any buffer solution contained therein during the collection of a fluid sample.

In an embodiment, the buffer tube 60 may be provided with a buffer tube lid 70. The buffer tube lid 70 may include the same or similar locking portion 40 (including one or more locking arms 42, each with one or more locking arm protrusions 44) and the same or similar seal member 50 to substantially contain any buffer solution and/or sample liquid within the buffer tube 60 while substantially preventing contamination. In an embodiment, following the collection of a fluid sample, the buffer tube 60 may be sealed with the locking portion 40 and seal 50 of either the buffer tube lid 70 or the handle 20 coupled to the collection portion 30.

The buffer solution provided, for example in buffer tube 60, may incorporate various components available as off the shelf reagents. Minimally the buffer may contain a lysis reagent to lyse the cells and a preservative agent to stabilize the components in the collected sample for a period of several months. Guanidine is one agent known to preserve genetic samples (e.g., DNA and/or RNA) for long periods of time. Other buffer solutions may be provided in or with buffer tube 60 consistent with an embodiment of fluid sample collection system 10.

The sample collection system 10 may include identification information so that the sample collection system 10 and the sample collected thereby may be uniquely identified and/or tracked. For example, the handle portion 20, sample portion 30, and/or buffer tube 60 of an embodiment may further include unique identification information. More specifically, the handle portion 20, sample portion 30, and/or buffer tube 60 may include a numeric identifier, serial number, linear bar code, matrix bar code or the like to uniquely identify the sample collection system 10 and sample collected thereby. Additionally, the handle portion 20 and/or the buffer tube 60 may include means by which one or more fingerprints may be collected. For example, the handle portion 20 and/or the buffer tube 60 may include a material, surface, compound, or the like on or in which a sample source may depress a finger or thumb to record their finger or thumbprint.

In operation in one embodiment, a sample collector may be provided with a buffer tube 60 containing buffer solution. The buffer tube 60 may be substantially sealed with a buffer tube lid 70. The sample collector may set the buffer tube 60 on a flat surface such that it is sitting substantially upright on the flange stand 66. Thereafter, the sample collector may remove and discard the buffer tube lid 70.

To collect the sample fluid, the sample collector may scrape, swipe, and/or swab the collection portion 30 against, for example, a tongue to collect saliva. In an embodiment, the saliva may be collected in one or more holes 32, on one or more protrusions 34, or a combination thereof. The sample collector may then insert at least the collection portion 30 into the buffer tube 60 until it removably locks into place with the engagement of the locking arm protrusions 44 and the buffer tube dimples 62 and seals with the engagement of the seal member 50 and the interior of the buffer tube 60 (e.g., against the seal shoulder 64). The sample collector may then vigorously shake the fluid sample collection system 10 to extract the sample fluid, for example saliva, from the collection portion 30. In an embodiment, the sample collector may then break off at least a portion of handle 20. The fluid sample collection system 10 as a complete unit or at least partially without handle 20 may then be sent to a laboratory or other site for the purpose of DNA or RNA extraction and/or subsequent processing and analysis.

Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

We claim:

1. An apparatus, comprising:
   a handle having a first end and a second end:
   a collector portion coupled to the second end of the handle at a junction, the collector portion comprising opposed first and second surfaces, each of the first surface and second surfaces having a corresponding first and second plurality of protrusions distributed on the respective surface, each protrusion extending outward from the corresponding first or second surface to a distal end;
   a buffer tube including an internal cavity adapted to removably receive at least the collector portion therein, the buffer tube further including a buffer solution contained within the internal cavity;
   a locking portion coupled to the handle proximate the junction of the handle and collector portion, the locking portion including a locking member removably engageable to the buffer tube and a seal member adapted to sealingly engage the buffer tube internal cavity when the collector portion is inserted into the internal cavity.

2. The apparatus of claim 1, the locking member further comprising one or more locking arms extending laterally from the locking portion.

3. The apparatus of claim 2, the one or more locking arms each further comprising one or more locking arm protrusions to engage one or more buffer tube dimples formed in the buffer tube.

4. The apparatus of claim 1, the buffer tube further comprising a seal shoulder to detachably engage the seal member.

5. The apparatus of claim 1, the buffer tube further comprising a flange stand to stand the buffer tube substantially upright.

6. The apparatus of claim 1 further comprising a buffer tube lid to detachably engage the buffer tube and seal the internal cavity.

7. A apparatus as in claim 1, further comprising:
   wherein at least some protrusions in each of the first and second plurality of protrusions include corresponding open channels extending through each such protrusion, each open channel extending from the respective protrusion distal end through the opposed second surface.

8. A apparatus as in claim 7, further comprising:
   wherein the first and second pluralities of protrusions comprise symmetrical patterns aligned with each other on their respective opposed surfaces, and further wherein each of the corresponding open channels extends from the respective protrusion distal end through the distal end of a corresponding protrusion on the opposed surface.

9. A apparatus as in claim 1, further comprising:
   wherein at least some protrusions in each of the first and second plurality of protrusions include a dimple disposed at the respective protrusion distal end.

10. A apparatus as in claim 8, further comprising:
    wherein at least some protrusions in each of the first and second plurality of protrusions include a dimple disposed at the respective protrusion distal end.

* * * * *